United States Patent [19]

Soldati et al.

[11] 4,022,787
[45] May 10, 1977

[54] ANTICHOLINERGIC ESTER AND SALTS THEREOF

[75] Inventors: Gianluigi Soldati, Mercerville; Paul Finkelstein, Princeton Junction, both of N.J.; David A. Schlichting, Pound Ridge, N.Y.; William Oroshnik, Plainfield, N.J.

[73] Assignee: Carter-Wallace, Inc., New York, N.Y.

[22] Filed: July 18, 1975

[21] Appl. No.: 597,246

[52] U.S. Cl. .......................... 260/293.81; 424/267
[51] Int. Cl.² ...................................... C07D 211/46
[58] Field of Search ............................. 260/293.81

[56] References Cited

UNITED STATES PATENTS 2,680,765   6/1954   Sprague et al. .............. 260/293.81

FOREIGN PATENTS OR APPLICATIONS 1,032,646   6/1966   United Kingdom

OTHER PUBLICATIONS

Chemical Abstracts, vol. 79 (1973) 111685C.

*Primary Examiner*—Norma S. Milestone
*Attorney, Agent, or Firm*—Kevin B. Clarke

[57] ABSTRACT

N-methyl-4-piperidinyl-α-benzoyloxy-α-cyclopentylphenylacetate. The novel ester in the form of its free base or as a salt has been found to be an effective inhibitor of perspiration.

7 Claims, No Drawings

ANTICHOLINERGIC ESTER AND SALTS THEREOF

Sweat glands are activated by a chemical mediator usually considered to be acetylcholine which is liberated at cholinergic end organs when they are properly stimulated. An anticholinergic compound is one which antagonizes the action of acetylcholine probably by blocking the receptor sites of the secretory cells of the sweat glands so that the cells are unable to respond.

Drugs of the scopolamine and atropine-alkaloid series are classic members of the anticholinergic group. The usefulness of these drugs are diminished by the fact that they effect many organs simultaneously. Small doses effect salivary, bronchial and sweat secretions; larger doses cause the pupil to dilate, inhibit accommodation of the eye, and could cause gastrointestinal and urinary discomfort. An example of a scopolamine derivative found to be valuable for sweat inhibition is the benzoyl ester of scopolamine.

Since most of these drugs are capable of producing undesirable side effects, they usually are not suitable for cosmetic use.

An object of this invention is to provide a novel anticholinergic material which will safely and effectively reduce perspiration.

A further object of this invention is to provide an effective antiperspirant formulation which does not require astringent salts and which does not cause fabric damage, skin irritation and undue difficulties in formulation of a cosmetic product.

It was found that these and other objects are accomplished with an antiperspirant composition containing as active ingredient a novel anticholinergic compound of general formula:

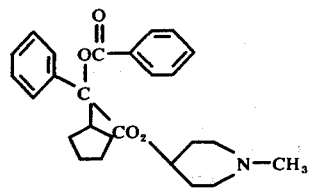

The compound, N-methyl-4-piperidinyl α-benzoyloxy-α-cyclopentyl-phenylacetate, can be in the form of the free base or as a salt such as an hydrochloride, hydrobromide, sulfate, acetate, laurate, gluconate, maleate, methiodide, methochloride, methobromide, pentylbromide, dodecylbromide, phosphate.

The drug was investigated as an anticholinergic antiperspirant. A test to demonstrate the anticholinergic effect of the compounds referred to herein was conducted in rabbit eyes.

One eye of each animal was treated with a drop of 6% pilocarpine solution. Fifteen minutes later, the test compound was applied to the eye. Measurements of pupil dilation were taken and the effect of the test compound established. No unusual side effects were noticed.

The following data represent measurements of the rabbit eye pupil. Units are expressed in millimeters. Treated eye received 6% pilocarpine, one drop, at 15 minutes prior to first reading. Test compound was given at zero time just prior to reading.

Only one concentration of test material was administered, and all experiments were conducted under normal room light conditions. Four rabbits were used in the experiment.

The single dose I.P. toxicity of the test compound, (the preferred form being the hydrochloride salt) in albino mice was determined to be 61 mg/kg for the $LD_{50}$ value. The single dose oral toxicity of the aforementioned test compound in albino mice was determined to be 310 mg/kg for the $LD_{50}$ value.

| Animal No. | % Conc. | Eye | −15 | −10 | −5 | 0 | +5 | +10 | +15 | +20 | +25 | +30 | +35 | +40 | +45 | +50 | +55 | +60 | +65 |
|---|---|---|---|---|---|---|---|---|---|---|---|---|---|---|---|---|---|---|---|
| 1 | 0.6 | T* | 4 | 4 | 3 | 3 | 3 | 3.5 | 3.5 | 4 | 4 | 5 | 5 | 5.5 | 5.5 | 5 | 5 | 5 | 5 |
|   |     | U  | 5 | 5 | 5 | 6 | 5.5 | 5.5 | 5.5 | 5.5 | 6 | 5.5 | 6.5 | 6 | 5.5 | 5.5 | 5.5 | 5 | 5 |
| 2 | 0.6 | T  | 6 | 5 | 3 | 3 | 4 | 6.5 | 7 | 6.5 | 5.5 | 6.5 | 6 | 6 | 6.5 | 6.5 | 6.5 | 7 | 6.5 |
|   |     | U  | 6 | 5 | 5 | 5.5 | 6 | 6 | 6 | 6 | 5.5 | 6 | 6.5 | 6.5 | 6 | 6.6 | 6.5 | 6.5 | 6.5 |
| 3 | 0.6 | T  | 9 | 7.5 | 6 | 5 | 6 | 7.5 | 7.5 | 8 | 7.5 | 8 | 8 | 8.5 | 8.5 | 8.5 | 8.5 | 8.5 | 8.5 |
|   |     | U  | 10 | 9 | 8 | 7.5 | 6.5 | 8 | 8 | 8 | 9 | 8.5 | 8.5 | 9 | 9 | 9 | 9 | 9 | 8.5 |
| 4 | 0.6 | T  | 7 | 7.5 | 6.5 | 6 | 7.5 | 7 | 7.5 | 8 | 8.5 | 7.5 | 8 | 7.5 | 8 | 8 | 8 | 8 | 8 |
|   |     | U  | 6.5 | 6 | 6 | 6.5 | 7 | 7 | 7 | 7.5 | 7 | 7.5 | 7.5 | 7.5 | 7 | 8 | 8 | 8 | 8 |

*T-treated; U-untreated
Atropine sulfate 0.6% gave similar results

The test compound was applied topically for seven consecutive days up to 160 micrograms/kg of body weight to human skin. No definite side effects were observed. In later testing the dose was increased to 320 and 640 micrograms/kg without definite signs of side effects. EKG's were taken before and after application of the two highest doses of the novel composition. No drug effects were elicited. An antiperspirant back test was conducted with concentration of the test compound of up to 4% in a 75% alcoholic solution. The product was demonstrated to be significantly effective.

The novel compositions referred herein are prepared by the reaction of methyl α-phenyl-α-cyclopentyl glycolate and N-methyl piperidinol in the absence of moisture. The reaction occurs by transesterification according to the following equation.

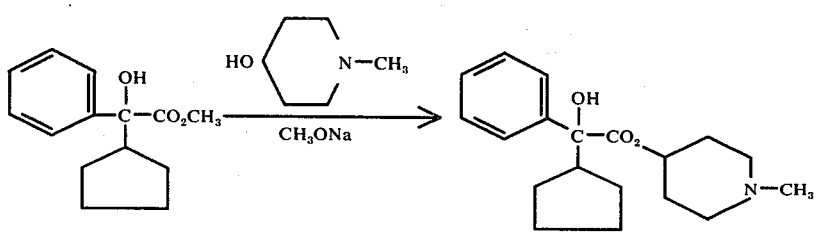

The second step of the reaction involves the benzoylation of compound (1) with benzoyl chloride in presence of methyl lithium.

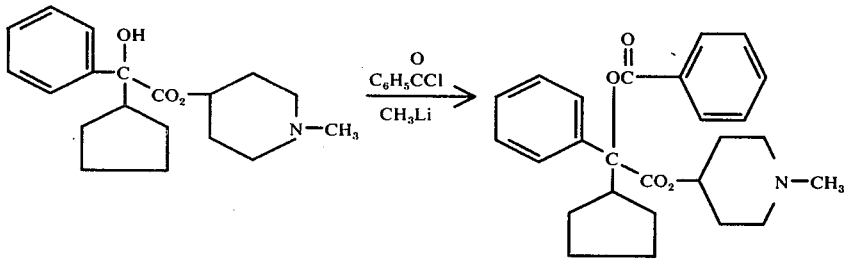

The sequence in step (1) presents no novel chemistry but only economic application of the known arts. In step (2), on the other hand, we have, by working at low temperature, managed to localize the reaction of methyl lithium with the OH group of the molecule in the presence of another very reactive group, the ester group, on the molecule. The choice of the temperature of reaction permits this regional specificity even in the presence of an excess of methyl lithium. Secondly, by using an excess of benzoyl chloride at this low temperature, the excess of benzoyl chloride destroys the excess methyl lithium before it has a chance to react with the ester group as the reaction temperature is raised. This benzoylation is the only known one-step acylation on molecules containing two reactive groups. Previously reported methods of introduction of an acyl group into a basic ester of similar structure (J. Kosa and G. Delmar, *J. Prakt. chimie*, 16, 71–82 (1962)) involve a multi-step sequence.

The following examples, for illustrative purposes only, show how the novel compound of this invention, its salts and substituents thereof may be prepared. In addition example VII describes basic formulations in which the active antiperspirant ingredient thereof are the compositions which are the subject of this patent.

EXAMPLE I

N-METHYL-4-PIPERIDINYL α-BENZOYLOXY-α-CYCLOPENTYL-PHENYLACETATE HYDROBROMIDE HYDROCHLORIDE SALT.

Methyl α-cyclopentyl-α-phenyl glycolate (233 g.), N-methylpiperidin-4-ol (115 g.), Heptane (b.p. 94–95) 1540 ml, and Sodium methoxide (9.1 g.) are slowly distilled until the methanolheptane azeotrope no longer came over as shown by the take-off temperature reaching and staying at 94° (3 hrs.). The mixture was then cooled and poured into 1 liter of water and shaken vigorously. The heptane phase was separated and washed successively, with water until neutral and then dried over anhydrous magnesium sulfate, filtered and concentrated under vacuum.

The concentrate was dissolved in one liter of dry methylene chloride and hydrochloric acid passed in at 0° with external cooling until saturated. The solution was then concentrated under vacuum to remove the excess of acid and the concentrate redissolved in 1300 ml of warm methylene chloride. Approximately 2000 ml of acetone was then added and the solvent boiled off until crystals began to appear. The mixture was allowed to cool slowly to 25° and then stored overnight at 3° to complete precipitation of the product.

The precipitate was filtered off and washed with cold acetone (−10°) (3 × 200 ml) and dried under vacuum.

The combined filtrate and washings were concentrated to 500 ml under slight vacuum. The mixture was allowed to cool slowly and then set in the refrigerator overnight. The next day it was filtered and the product washed with cold acetone (−10°) (3 × 71 ml). The product was dried under vacuum. Yield; Crop I: 228.1 g.; m.p. 223.5–225.5, Crop II: 51.1 g.; m.p. 221–223.

The product obtained from the reaction described above (279 g.) was placed in a 3. l. flask containing 1 l. of 25% aqueous $K_2CO_3$ and 1 l. of pentane. The mixture was stirred mechanically at high speed until the suspended hydrochloride dissolved (4 hrs.). The pentane layer was separated, dried over potassium carbonate, filtered and concentrated under vacuum. The concentrate was transferred to a 5-l. three necked flask with benzene (250 ml) and the benzene boiled off under vacuum, thus assuring anhydrous conditions.

Anhydrous ether (3.0l.) was then added and the mixture stirred until solution was complete. The solution was then cooled to −35° and, with good stirring, 477 ml. of $CH_3Li$ (1.8 M in ether) were added dropwise. The temperature was maintained at −30° throughout the addition with a dry ice-acetone bath (2–3 hrs.). The benzoyl chloride (209 ml) was then added at −30° and the mixture stirred an additional 15 min. at this temperature. The cooling bath was removed and the stirring mixture allowed to reach 25° and then set to stand overnight.

The mixture was now cooled to 0°, and with good stirring 800 ml. of water added dropwise. Upon complete addition, the ether was removed under vacuum and replaced with one liter of methylene chloride. The latter was then separated, dried over $MgSO_4$, filtered and concentrated back to one liter.

Gaseous hydrochloric acid was passed into the methylene chloride solution at 0° until saturated. The excess HCl and the solvent were then removed under vacuum. One liter of anhydrous ether was then added to the syrup and the mixture stirred mechanically. Crystallization soon commenced. After 2 hours of stirring the mixture was filtered and the product washed with ether (3 × 300 ml.) and dried under vacuum. Yield: 387.4 g.; m.p. 180°–184°.

The product was recrystallized by solution in 1130 ml. of methylene chloride followed by addition of 2400 ml. of dry ether. Precipitation began within minutes following the addition of the ether.

After standing two days, the mixture was filtered and the product washed with a mixture of ether-$CH_2Cl_2$ (2:1) (3 × 300 ml.). The product was dried under vacuum. Yield: 322.7 g.; m.p. 185°–187°.

ANALYSIS

Calculated (%) for $C_{26}H_{31}NO_4$ 73% HBr. 27% HCl: C 63.67; H 6.57; N 2.86; O 13.05; Br 11.89; Cl 1.95. Found %: C 63.48; H 6.66; N 2.80; O 12.88; Br 11.81; Cl 1.86.

EXAMPLE II

N-METHYL-4-PIPERIDINYL α-BENZOYLOXY-α-CYCLOPENTYL-PHENYLACETATE 10 g. of the above salt are slurried in 100 ml of ethyl ether and 100 ml. of 10% aqueous sodium bicarbonate. As soon as two clear phases form, the mixture is transferred to a separatory funnel and the ethereal phase separated and dried over anhydrous magnesium sulfate. Evaporation of the ether yields a highly viscous oil in almost quantitative yield. The material gave the following analysis after elution with $CHCl_3$:$CH_3OH$(4:1) through an 11 inch × 1 inch silica gel column.

ANALYSIS

Calculated (%) for $C_{26}H_{31}NO_4$: C74.08; H 7.41; N 3,32; O 15.18. Found %: C73.83; H 7.42; N 3.40; O 15.02.

EXAMPLE III

N-METHYL-4-PIPERIDINYL α-BENZOYLOXY-α-CYCLOPENTYL-PHENYLACETATE ACETATE 6.7 g. of product obtained as described in Example II is dissolved in 100 ml. of anhydrous ether and treated with 0.95 g. of glacial acetic acid. The solvent is removed and replaced with petroleum ether. The gummy residue slowly crystallizes to give crystals melting at 78°–80°. I.R. is in accordance with the anticipated structure. Yield 4 g.

EXAMPLE IV

N-METHYL-4-PIPERIDINYL α-BENZOYLOXY-α-CYCLOPENTYL-PHENYLACETATE HYDROBROMIDE

The free base obtained as described in Example II from 10 g. of N-methyl-4-piperidinyl-α-benzoyloxy-α-cyclopentyl-phenylacetate hydrochloride-hydrobromide salt is dissolved in 200 ml. of a 50-50 mixture of methylene chloride-ethyl ether. Gaseous hydrobromic acid is passed through the solution until strong acid reaction to Hydrion paper. The solvent is then evaporated under reduced pressure and the viscous residue covered with anhydrous ether for two days. The oil solidifies on standing after addition of some methylene chloride. The product is collected, and crystallized with 30 ml methylene chloride and 60 ml of ether. The 4.6 g. of product are recrystallized twice from methylene chloride-ether. Mp. 185°–186.5°.

Calculated (%) for $C_{26}H_{31}NO_4$ HBr; C 62.15; H 6.42; N 2.78; Br 15.92. Found (%): C 61.56; H 6.50; N 2.87; Br 15.23.

EXAMPLE V

N-METHYL-4-PIPERIDINYL α-BENZOYLOXY-α-CYCLOPENTYL-PHENYLACETATE HYDROCHLORIDE 8.3 g. of the free base obtained as described in Example II are dissolved in 200 ml of methylene chloride and 100 ml of ether. Gaseous Hydrogen chloride is passed in at 0°–10° until saturated. The solvent and the excess of acid are removed under reduced pressure and the viscous residue covered with anhydrous ether. After few hours the ether is decanted, and the syrup recovered with ether. After 24 hours the crystallization is complete. Yield 8 g. Recrystallized three times from methylene chloride-ether the white crystalline material melts at 162.5°–164°.

ANALYSIS:

Calculated (%) for $C_{26}H_{31}NO_4$ HCl: C 68.18; H 7.04; N 3.05; Cl 7.74 Found %: C 67.87; H 6.97; N 3.23; Cl 7.53.

EXAMPLE VI

N-METHYL-4-PIPERIDINYL α-BENZOYLOXY-α-CYCLOPENTYL-PHENYLACETATE METHIODIDE 5 g of N-methyl-4-piperidinyl α-benzoyloxy-α-cyclopentyl-phenylacetate hydrochloride are dissolved in 30 ml of water. 50 ml. of ether are added and the mixture slowly neutralized with 10% aqueous potassium carbonate. The ethereal phase is then separated, dried over anhydrous magnesium sulfate, filtered and evaporated. The residue is dissolved in 10 ml. of anhydrous acetone and methyl iodide (2 g.) is added. The solution is refluxed for four hours. After cooling ether is added to precipitate the product. 5 g. of material are thus obtained. Recrystallized from methanol-ether. Mp. 133°–7°.

ANALYSIS:

Calculated (%) for $C_{27}H_{34}NIO_4$: C 57.55; H 6.08; N 2.50 Found (%): C 57.68; H 6.27; N 2.42.

EXAMPLE VII

The following lotions containing the compound of this invention, in the hydrochloride form, as the active antiperspirant ingredient, are given as an example only, and they are not to be considered limiting or binding.

|  | I | II | III |
|---|---|---|---|
| Compound II HCl | 0.50 | 0.25 | 0.25 |
| SD-40 95% | 50.00 | 50.00 | 50.00 |

| | I | II | III |
|---|---|---|---|
| Water | 48.70 | 48.95 | 47.95 |
| Methocel 65HG4000 | 0.80 | 0.80 | 0.80 |
| Igepal CO 630 | — | — | 1.00 |

What is claimed is:

1. N-methyl-4-piperidinyl α-benzoyloxy-α-cyclopentyl-phenylacetates of formula:

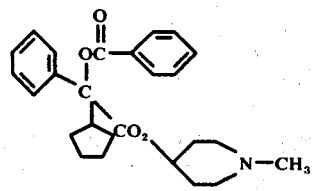

in the form of the free base or as a salt such as the hydrochloride, hydrobromide, hydroiodide, sulfate, acetate, phosphate, gluconate, laurate, maleate, methochloride, methobromide, methiodide, pentylbromide or dodecylbromide.

2. N-methyl-4-piperidinyl α-benzoyloxy-α-cyclopentyl-phenylacetate.

3. N-methyl-4-piperidinyl α-benzoyloxy-α-cyclopentyl-phenylacetate hydrochloride.

4. N-methyl-4-piperidinyl α-benzoyloxy-α-cyclopentyl-phenylacetate hydrobromide.

5. N-methyl-4-piperidinyl α-benzoyloxy-α-cyclopentyl-phenylacetate acetate.

6. N-methyl-4-piperidinyl α-benzoyloxy-α-cyclopentyl-phenylacetate hydrobromide-hydrochloride.

7. N-methyl-4-piperidinyl α-benzoyloxy-α-cyclopentyl-phenylacetate methiodide.

* * * * *